(12) United States Patent
Narisawa

(10) Patent No.: US 11,974,766 B2
(45) Date of Patent: May 7, 2024

(54) TREATMENT TOOL AND METHOD OF MANUFACTURING TREATMENT TOOL

(71) Applicant: OLYMPUS CORPORATION, Hachioji (JP)

(72) Inventor: Masato Narisawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/871,046

(22) Filed: Jul. 22, 2022

(65) Prior Publication Data

US 2022/0354521 A1 Nov. 10, 2022

Related U.S. Application Data

(63) Continuation of application No. PCT/JP2020/003280, filed on Jan. 29, 2020.

(51) Int. Cl.
*A61B 17/28* (2006.01)
*A61B 17/29* (2006.01)
*A61B 17/32* (2006.01)

(52) U.S. Cl.
CPC .... *A61B 17/282* (2013.01); *A61B 2017/2825* (2013.01); *A61B 2017/2926* (2013.01);
(Continued)

(58) Field of Classification Search
CPC .......... A61B 17/282; A61B 2017/2937; A61B 2017/320094; A61B 17/320092;
(Continued)

(56) References Cited

U.S. PATENT DOCUMENTS 7,264,618 B2 * 9/2007 Murakami ............... A61N 7/02
606/45
7,306,599 B2 * 12/2007 Karasawa ............ A61B 18/085
606/50
(Continued)

FOREIGN PATENT DOCUMENTS

JP 2000-033092 A 2/2000
JP 2019-520913 A 7/2019
(Continued)

OTHER PUBLICATIONS

Apr. 14, 2020 International Search Report issued in International Patent Application No. PCT/JP2020/003280.

*Primary Examiner* — Shaun L David
*Assistant Examiner* — Mitchell Brian Hoag
(74) *Attorney, Agent, or Firm* — Oliff PLC

(57) ABSTRACT

A treatment tool includes a first grasper and a second grasper. The first grasper includes a treatment portion that includes a treatment surface and an opposing surface, and a holder portion that is mounted on the opposing surface. The holder portion is formed of an elastically deformable material, and includes a first region having a first contact surface, a second region having a second contact surface, and a connection region that is arranged between the first contact surface and the second contact surface and that includes a concave portion. The holder portion is mounted on the opposing surface in an elastically deformed state such that the first contact surface and the second contact surface are in contact with the opposing surface and such that a depth of the concave portion is smaller than a depth of the concave portion is a non-elastically deformed state.

13 Claims, 11 Drawing Sheets

(52) U.S. Cl.
CPC ............... *A61B 2017/2929* (2013.01); *A61B 2017/2936* (2013.01); *A61B 2017/2937* (2013.01); *A61B 17/320092* (2013.01); *A61B 2017/320094* (2017.08)

(58) Field of Classification Search
CPC .... A61B 2017/2825; A61B 2017/2926; A61B 2017/2936; A61B 17/320068
USPC .......................................................... 606/207
See application file for complete search history.

(56) References Cited

U.S. PATENT DOCUMENTS

| | | | |
|---|---|---|---|
| 8,518,067 B2* | 8/2013 | Masuda | A61B 17/320092 606/169 |
| 8,882,799 B2* | 11/2014 | Frank | A61B 17/062 606/174 |
| 9,282,990 B2* | 3/2016 | Yamada | A61B 18/1445 |
| 9,636,136 B2* | 5/2017 | Kawaguchi | A61B 90/03 |
| 2015/0148834 A1* | 5/2015 | Gee | A61N 7/00 606/169 |
| 2015/0164532 A1* | 6/2015 | Faller | A61B 17/320092 606/169 |
| 2015/0374428 A1* | 12/2015 | Sobajima | A61B 90/03 606/41 |
| 2017/0224410 A1* | 8/2017 | Takei | A61B 18/1445 |
| 2017/0265930 A1* | 9/2017 | Hirai | A61B 17/320068 |
| 2018/0000506 A1 | 1/2018 | Hibner | |

FOREIGN PATENT DOCUMENTS

| | | | | |
|---|---|---|---|---|
| WO | WO-2018131125 A1 * | 7/2018 | ............ | A61B 17/29 |
| WO | 2020/008530 A1 | 1/2020 | | |

* cited by examiner

TREATMENT TOOL AND METHOD OF MANUFACTURING TREATMENT TOOL

CROSS-REFERENCE TO RELATED APPLICATION

This application is a continuation of International Application No. PCT/JP2020/003280, filed on Jan. 29, 2020, the entire contents of which are incorporated herein by reference.

BACKGROUND

1. Technical Field

The present disclosure relates to a treatment tool and a method of manufacturing the treatment tool.

2. Related Art

In the related art, a treatment tool that performs treatment on a living tissue by applying treatment energy to a region (hereinafter, described as a target region) that is a target for treatment the living tissue has been known.

In the treatment tool, ultrasound energy is adopted as the treatment energy. Specifically, the treatment tool grasps the target region between a distal end of an ultrasound probe and a jaw. Further, the treatment tool performs treatment on the target region by applying ultrasound vibration to the target region from a distal end of the ultrasound probe.

Furthermore, in the treatment tool, a wiper structure is adopted in which the jaw is rotatably supported by a pivot pin in a substantially central portion of the jaw in a longitudinal direction.

SUMMARY

In some embodiments, a treatment tool includes: a first grasper; and a second grasper configured to grasp a living tissue with the first grasper. The first grasper includes a treatment portion that includes a treatment surface facing the second grasper and an opposing surface serving as an opposing side of the treatment surface, and a holder portion that is mounted on the opposing surface of the treatment portion. The holder portion is formed of an elastically deformable material, and includes a first region having a first contact surface in contact with the opposing surface, a second region having a second contact surface in contact with the opposing surface, and a connection region that is arranged between the first contact surface and the second contact surface and that includes a concave portion. The holder portion is mounted on the opposing surface in an elastically deformed state such that the first contact surface and the second contact surface are in contact with the opposing surface and such that a depth of the concave portion is a second depth that is smaller than a first depth of the concave portion in a non-elastically deformed state. The holder portion is mounted on the opposing surface so as to be capable of further elastic deformation to a state in which the depth of the concave portion is less than the second depth.

In some embodiments, provided is a method of manufacturing a treatment tool that includes a treatment portion including a treatment surface and an opposing surface disposed on opposite sides of the treatment portion, and a holder portion that includes a first region having a first contact surface in contact with the opposing surface, a second region having a second contact surface in contact with the opposing surface, and a connection region that is arranged between the first contact surface and the second contact surface and that includes a concave portion. The method includes: arranging the holder portion such that the first contact surface and the second contact surface are in contact with the opposing surface; setting the holder portion in a first state in which the holder portion is elastically deformed into a state in which a depth of the concave portion is reduced from a first depth in a non-elastically deformed state to a second depth that is smaller than the first depth; and arranging a restricting portion between the treatment portion and the holder portion to prevent the holder portion from returning to the non-elastically deformed state from the first state.

The above and other features, advantages and technical and industrial significance of this disclosure will be better understood by reading the following detailed description of presently preferred embodiments of the disclosure, when considered in connection with the accompanying drawings.

DETAILED DESCRIPTION

Modes for carrying out the disclosure (hereinafter, embodiments) will be described below with reference to the drawings. The disclosure is not limited by the embodiments described below. In addition, in description of the drawings, the same components are denoted by the same reference symbols.

Configuration of Treatment Tool.

Figure 1:
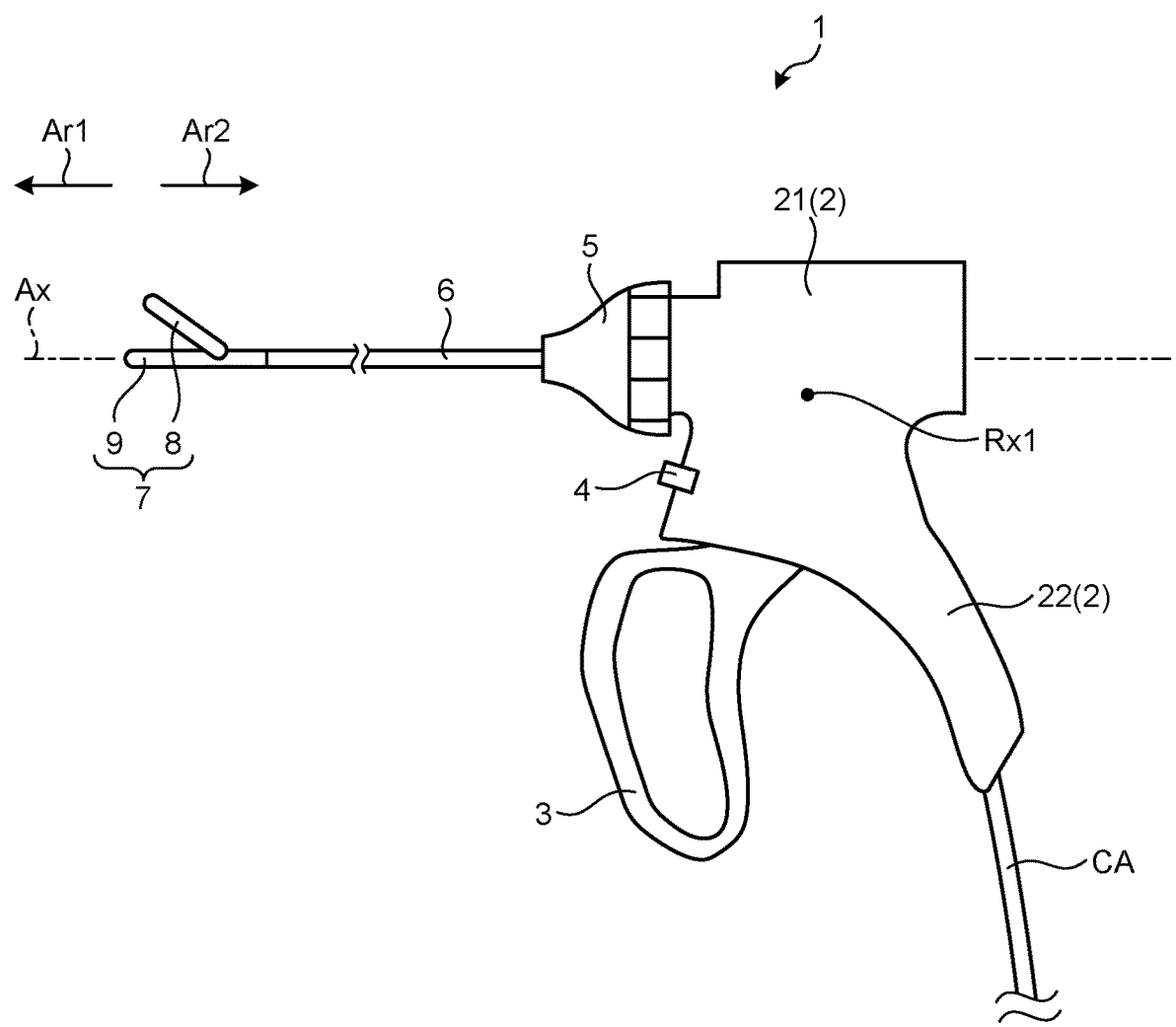
FIG. 1 is a diagram illustrating a configuration of a treatment tool according to an exemplary embodiment.

FIG. 1 is a diagram illustrating a configuration of a treatment tool 1 according to an exemplary embodiment.

In the following, for convenience of explanation, one end side along a central axis Ax of a sheath 6 is described as a distal end side Ar1, and the other side is described as a proximal end side Ar2 (FIG. 1).

The treatment tool 1 performs treatment on a region (hereinafter, descried as a target region) that s a target for treatment in a living tissue by applying treatment energy to the target region. In this embodiment, thermal energy is adopted as the treatment energy. Further, examples of the treatment include coagulation and incision of the target region. The treatment tool 1 includes, as illustrated in FIG. 1, a housing 2, a movable handle 3, a switch 4, a rotation knob 5, the sheath 6, and an end effector 7.

The housing 2 supports the entire treatment tool 1. As illustrated in FIG. 1, the housing 2 includes a housing main body 21 that is formed in an approximately shape that is coaxial with the central axis Ax, and a fixed handle 22 that extends from the housing main body 21 to a lower side in FIG. 1 and that is grasped by an operator.

The movable handle 3 is supported about an axis on the housing 2 so as to be rotatable about a first rotation axis Rx1 that is perpendicular to the sheet of FIG. 1. Further, the movable handle 3 receives open-close operation performed by the operator. The open-close operation is operation of rotating the movable handle 3 about the first rotation axis Rx1 relative to the housing 2.

As illustrated in FIG. 1, the switch 4 is arranged so as to be exposed Co outside from a side surface of the fixed handle 22 on the distal end side Ar1, and receives output start operation performed by the operator. The output start operation is operation of pressing the switch 4, and is operation of starting to apply the treatment energy to the target region. Further, the switch 4 outputs an operation signal corresponding to the output start operation to a control device (not illustrated) via an electrical cable CA (FIG. 1).

The rotation knob 5 has an approximately cylindrical shape that extends along the central axis Ax, and is supported by the housing main body 21 so as to be rotatable about the central axis Ax in a posture in which the rotation knob 5 is coaxial with the central axis Ax. Further, the rotation knob 5 receives rotation operation performed by the operator. With the rotation operation, the rotation knob 5 rotates about the central axis Ax relative to the housing main body 21.

The entire sheath 6 has an approximately cylindrical shape. As illustrated in FIG. 1, the end effector 7 is arranged on an end portion of the sheath 6 on the distal end side Ar1. Further, in the sheath 6, a part of an open-close mechanism (not illustrated) is inserted that opens and closes a first grasper 8 and a second grasper 9, which are included in the end effector 7, in accordance with the open-close operation that is performed on the movable handle 3 by the operator. Furthermore, an end portion of the sheath 6 on the proximal end side Ar2 is inserted in the rotation knob 5, and fixed to an inner surface of the rotation knob 5 by welding or the like. In other words, the sheath 6 and the end effector 7 rotate about the central axis Ax together with the rotation knob 5, in accordance with the rotation operation that is performed on the rotation knob 5 by the operator.

The end effector 7 is a part that performs treatment on the target region by applying the thermal energy to the target region.

A detailed configuration of the end effector 7 will be described below.

Configuration of End Effector

Figure 2:
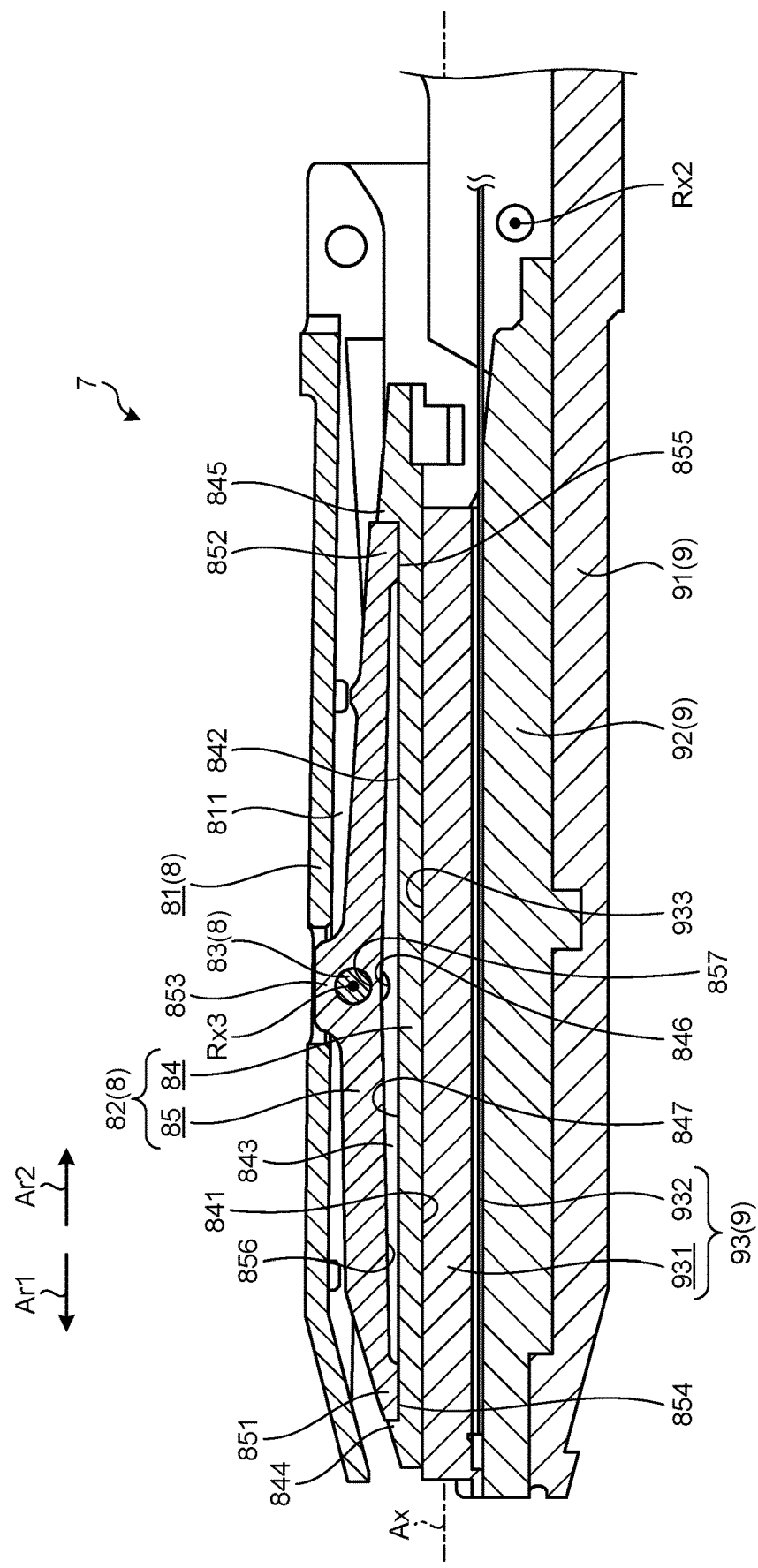
FIG. 2 is a diagram illustrating a configuration of an end effector.

FIG. 2 is a diagram illustrating the configuration of the end effector 7. Specifically, FIG. 2 is a cross-sectional view of the end effector 7 taken along a plane including the central axis Ax.

The end effector 7 includes the first grasper 8 and the second grasper 9 (FIG. 1 and FIG. 2) that are opened and closed when a driving force corresponding to the open-close operation that is performed on the movable handle 3 by the operator is transmitted via the open-close mechanism (not illustrated). Further, the first grasper 8 and the second grasper 9 grasp the target region by being opened and closed.

Configuration of Second Grasper

The second grasper 9 includes, as illustrated in FIG. 2, a second jaw 91, a support portion 92, and a treatment unit 93.

The second jaw 91 has an elongated shape that extends along the central axis Ax. Further, an end portion of the second jaw 91 on the proximal end side Ar2 is fixed to the end portion of the sheath 6 on the distal end side Ar1.

The support portion 92 is formed in an elongated shape that extends along the central axis Ax, and is fixed to an upper surface of the second jaw 91 in FIG. 2. The support portion 92 is configured with a material that has high heat resistant property and high thermal conductivity.

Electric power is supplied to the treatment unit 93 via the electrical cable CA under the control of an external control device (not illustrated). Further, the treatment unit 93 generates thermal energy in accordance with the electric power. The treatment unit 93 includes, as illustrated in FIG. 2, a blade 931 and a heater 932.

The blade 931 is configured with a material, such as copper, with high thermal conductivity, and has an elongated shape that extends along the central axis Ax.

In the blade 931, a surface 933 on an upper side in FIG. 2 is a surface that comes into contact with the target region while the first Grasper 8 and the second grasper 9 are grasping the target region, and that applies the thermal energy to the target region. In the following, for convenience of explanation, the surface 933 will be described as a second grasping surface 933. Meanwhile, "application of the thermal energy to the target region" means that heat is transmitted from the heater 932 to the target region.

Here, the second grasping surface 933 may be configured as a flat surface, or may be configured as a surface with a convex cross-sectional shape in which a central portion in a width direction (direction perpendicular to the sheet of FIG. 2) protrudes upward in FIG. 2.

As illustrated in FIG. 2, the heater 932 is arranged between the support portion 92 and the blade 931. The heater 932 includes two terminals, although detailed illustration is omitted. Lead wires as a pair included in the electrical cable CA are connected to the respective two terminals. Further, electric power is supplied to the heater 932 via the pair of lead wires under the control of an external control device (not illustrated). With this configuration, the heater 932 generates heat and heats the blade 931. Examples of the heater 932 include a sheet heater in which a metallic foil is patterned on a substrate that is made of polyimide or the like, a ceramic heater in which a platinum thin film is patterned on a ceramic substrate made of aluminum nitride or the like, and other printing heaters.

Configuration of First Grasper

The first grasper 8 includes, as illustrated in FIG. 2, a first jaw 81 and a wiper jaw 82.

The first jaw 81 corresponds to a jaw portion. The first jaw 81 has an elongated shape that extends along the central axis Ax. Further, an end portion of the first jaw 81 on the proximal end side Ar2 is supported about an axis on the second jaw 91 so as to be rotatable about a second rotation axis Rx2 (FIG. 2). Further, the first jaw 81 rotates about the second rotation axis Rx2 when a driving force corresponding to the open-close operation that is performed on the movable handle 3 by the operator is transmitted via the open-close mechanism (not illustrated). Accordingly, the first grasper 8 and the second grasper 9 are opened and closed. Meanwhile, the second rotation axis Rx2 is an axis that is perpendicular to a longitudinal direction (direction along the central axis Ax) that connects a distal end and a proximal end of the end effector 7.

In the first jaw 81, a pair of side wall portions 811 that face each other along a direction perpendicular to the sheet of FIG. 2 is arranged on a lower surface in FIG. 2. Meanwhile, in FIG. 2, of the pair of the side wall portions 811, only the first side wall portion 811 on the far side of the sheet of FIG. 2 is illustrated.

In the side wall portions 811 as the pair, first circular holes 812 (see FIG. 6) that penetrate through the side wall portions 811 along a direction perpendicular to the sheet of FIG. 2 are arranged at opposing positions.

The wiper jaw 82 has an elongated shape that extends along the central axis Ax, is arranged between the pair of side wall portions 811, and is mounted on the pair of side wall portions 811 by a rotation shaft part 83 (FIG. 2).

Here, the rotation shaft part 83 has a columnar shape that extends along a third rotation axis Rx3 (FIG. 2) and that has an outer diameter size that is slightly smaller than an inner diameter size of each of the first circular holes 812, and is inserted in each of the first circular holes 812. Further, the rotation shaft part 83 allows the wiper jaw 82 to rotate about the third rotation axis Rx3 relative to the first jaw 81. Meanwhile, the third rotation axis Rx3 corresponds to a first axis and is an axis parallel to the second rotation axis Rx2.

A detailed configuration of the wiper jaw 82 will be described below.

Figure 3:
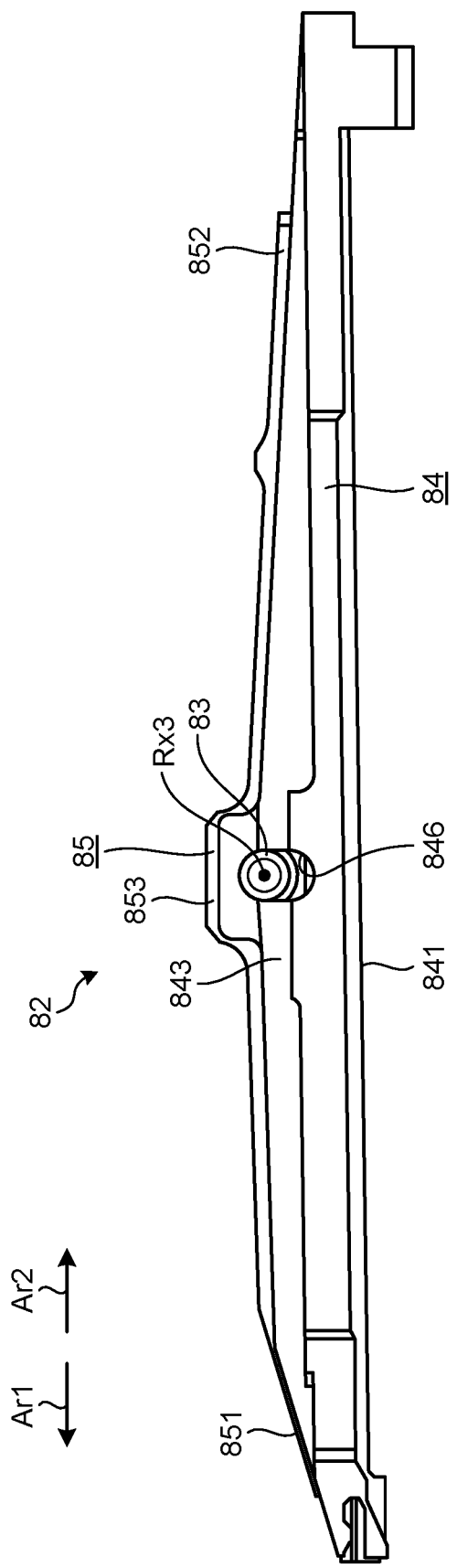
FIG. 3 is a diagram illustrating a configuration of a wiper jaw.
Figure 4:
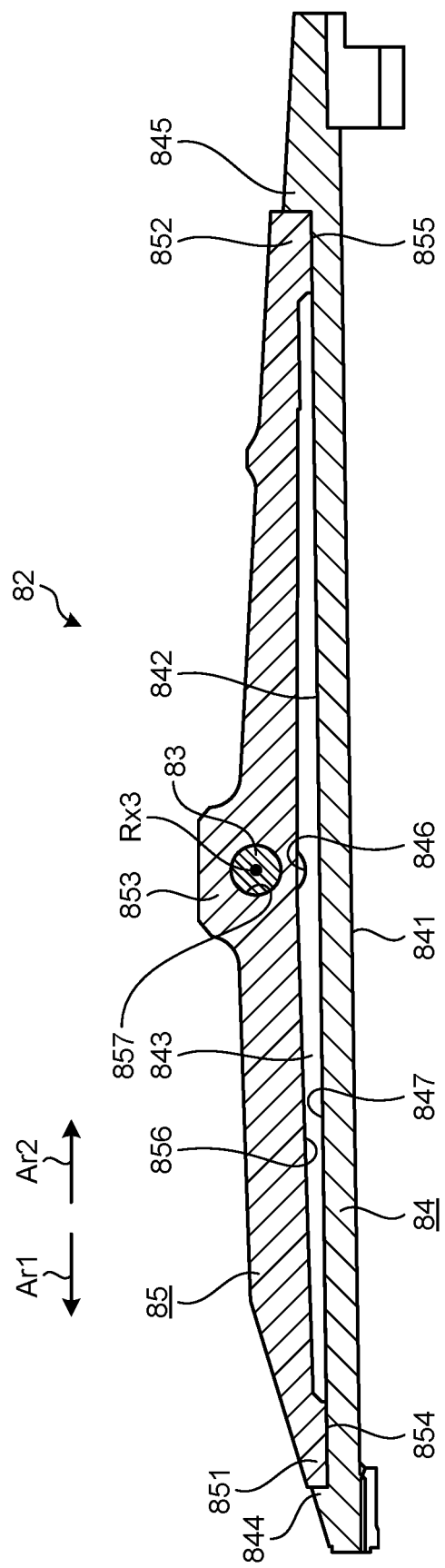
FIG. 4 is a diagram illustrating the configuration of the wiper jaw.

Configuration of Wiper Jaw FIG. 3 and FIG. 4 are diagrams illustrating the configuration of the wiper jaw 82. Specifically, FIG. 3 is a diagram of the wiper jaw 82 when viewed in the width direction (direction perpendicular to the sheet of FIG. 2). FIG. 4 is a cross-sectional view of the wiper jaw 82 in FIG. 3 taken along a plane including the central axis Ax.

As illustrated in FIG. 2 to FIG. 4, the wiper jaw 82 includes a treatment portion 84 and a holder portion 85.

The treatment portion 84 has an elongated shape that extends along the central axis Ax.

In the treatment portion 84, a surface 841 on a lower side in FIG. 3 and FIG. 4 is a surface that grasps the target region with the second grasping surface 933. In the following, for convenience of explanation, the surface 841 will be described as a first grasping surface 841. The first grasping surface 841 corresponds to a treatment surface.

Here, the first grasping surface 841 may be configured as a flat surface, or may be configured as a surface with a convex cross-sectional shape in which a central portion in a width direction (direction perpendicular to the sheet of FIG. 4) protrudes downward in FIG. 3 and FIG. 4 or a concave cross-sectional shape in which the central portion is recessed upward in FIG. 3 and FIG. 4.

Further, in the treatment portion 84, a surface 842 on an upper side in FIG. 4 is a surface that serves as an opposing side of the first grasping surface 841, and corresponds to an opposing surface. In the following, for convenience of explanation, the surface 842 will be described as the opposing surface 842.

The opposing surface 842 is configured as a flat surface. In the opposing surface 842, a pair of second side wall portions 843, a third side wall portion 844, and a fourth side wall portion 845 are arranged.

The pair of second side wall portions 843 corresponds to a pair of side wall portions. The second side wall portions 843 as the pair face each other along the direction perpendicular to the sheet of FIG. 4.

In the second side wall portions 843 as the pair, first long holes 846 that penetrate through the second side wall portions 843 along the direction perpendicular to the sheets of FIG. 3 and FIG. 4 are arranged at opposing positions.

Each of the first long holes 846 corresponds to a first hole. Each of the first long holes 846 is a hole that has approximately the same width as the inner diameter size of each of the first circular holes 812, and that extends in a vertical direction in FIG. 3 and FIG. 4. Further, the rotation shaft part 83 is inserted in the first long holes 846.

The third side wall portion 844 connect end portions of the second side wall portions 843 as the pair on the distal end side Ar1 and the fourth side wall portion 845 connect end portions of the second side wall portions 843 as the pair on the proximal end side Ar2.

In other words, on an upper side of the treatment portion 84 in FIG. 4, a first concave portion 847 is arranged in which four sides are enclosed by the pair of second side wall portions 843, the third side wall portion 844, and the fourth side wall portion 845 and the opposing surface 842 serves as a bottom surface.

The holder portion 85 has an elongated shape that extends along the central axis Ax, and is arranged so as to engage with the first concave portion 847 as illustrated in FIG. 4. Meanwhile, the holder portion 85 has an approximately the same cross-sectional shape over the entire length in the width direction (direction perpendicular to the sheet of FIG. 4).

The holder portion 85 includes, as illustrated in FIG. 4, a first region 851, a second region 852, and a connection region 853.

The first region 851 is a region That is located on the distal end side Ar1 in the holder portion 85, and includes a first contact surface 854 that comes into contact with the opposing surface 842 (FIG. 4). The first contact surface 854 is configured as a flat surface.

The second region 852 is a region that is located on the proximal end side Ar2 in the holder portion 85, and includes a second contact surface 855 that comes into contact with the opposing surface 842 (FIG. 4). The second contact surface 855 is configured as a flat surface.

The connection region 853 is a region that extends from the distal end side Ar1 to the proximal end side Ar2 at a position separated from the opposing surface 842, and that connects the first region 851 and the second region 852.

Further, in the holder portion 85, a second concave portion. 856 that is recessed in a direction away from the opposing surface 842 and that penetrates through the holder portion 85 in the direction perpendicular to the sheet of FIG. 4 is formed between the first contact surface 854 and the second contact surface 855. The second concave portion 856 corresponds to a concave portion.

Furthermore, a second circular hole 857 that penetrates through the connection region 853 along the direction perpendicular to the sheet of FIG. 4 is arranged in the connection region 853.

The second circular hole 857 corresponds to a second hole. The second circular hole 857 has the same inner diameter sire as the inner diameter sire of each of the first circular holes 812, In other words, each of the first long holes 846 is a hole that is larger than the second circular hole 857. Moreover, the rotation shalt part 83 is inserted in the second circular hole 857. In other words, the first jaw 81 supports the holder portion 85 in the connection region 853.

Method of Manufacturing Treatment Tool

Figure 5:
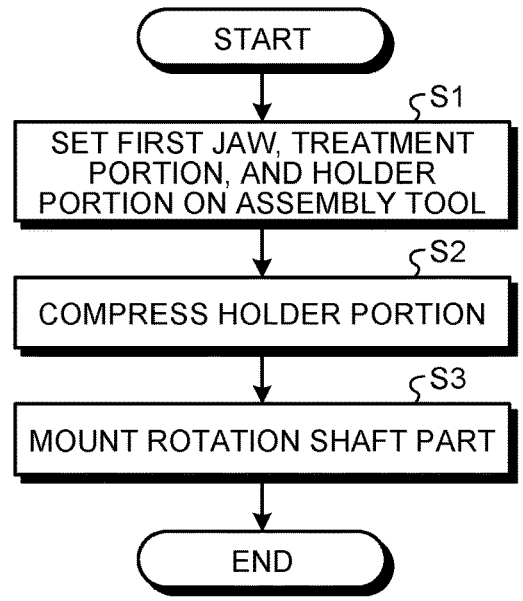
FIG. 5 is a flowchart illustrating a method of manufacturing the treatment tool.
Figure 6:
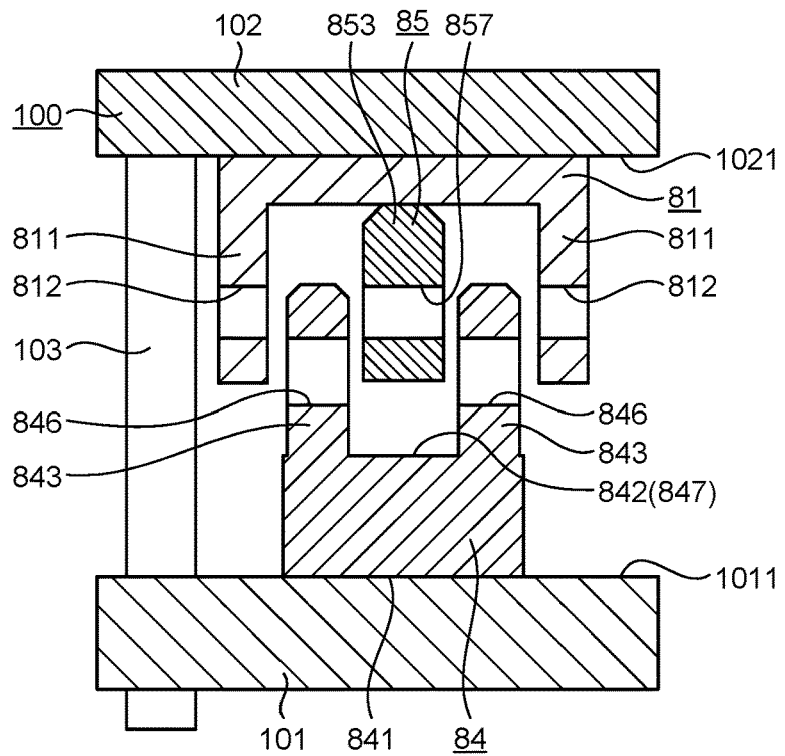
FIG. 6 is a diagram for explaining the method of manufacturing the treatment tool.
Figure 7:
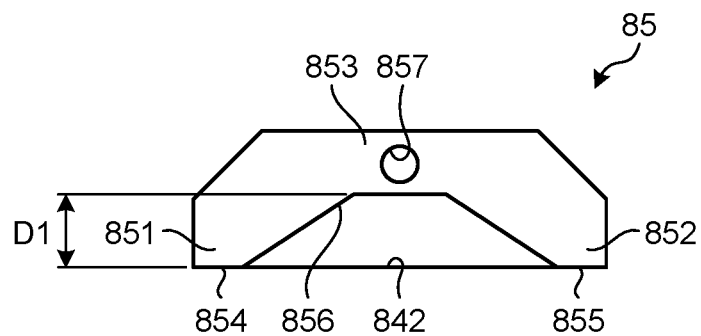
FIG. 7 is a diagram for explaining the method of manufacturing the treatment tool.
Figure 8:
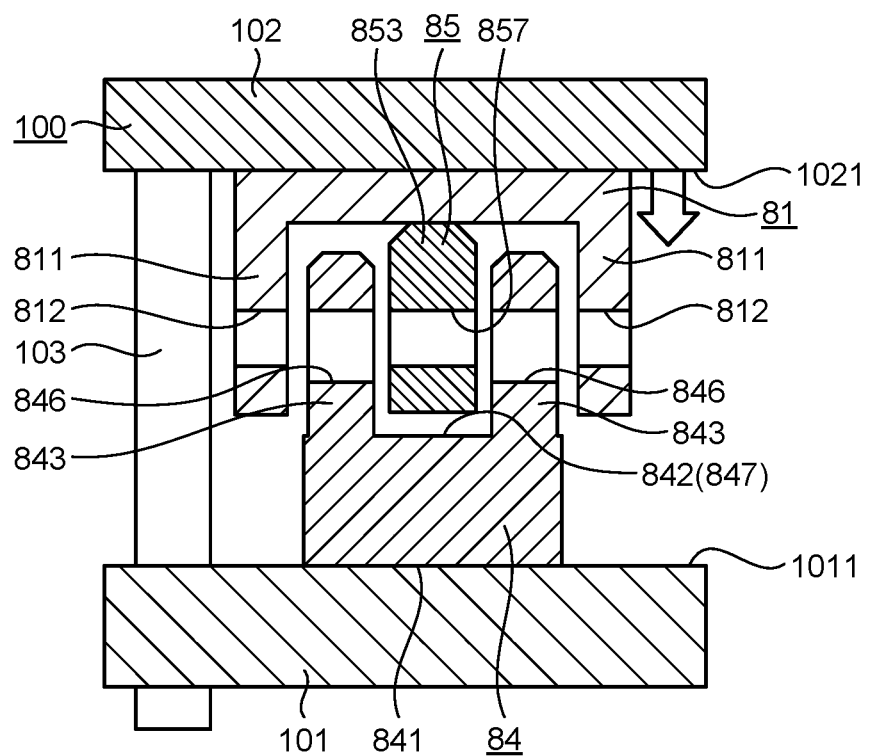
FIG. 8 is a diagram for explaining the method of manufacturing the treatment tool.
Figure 9:
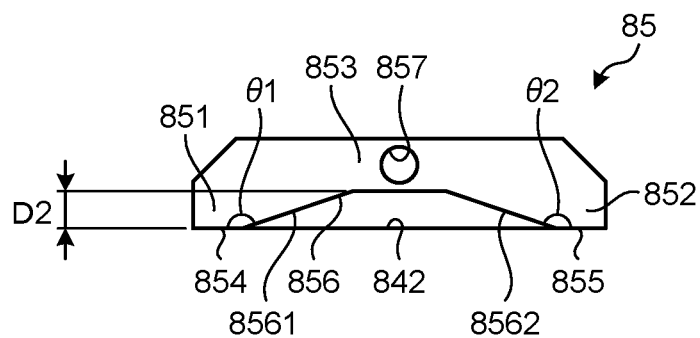
FIG. 9 is a diagram for explaining the method of manufacturing the treatment tool.
Figure 10:
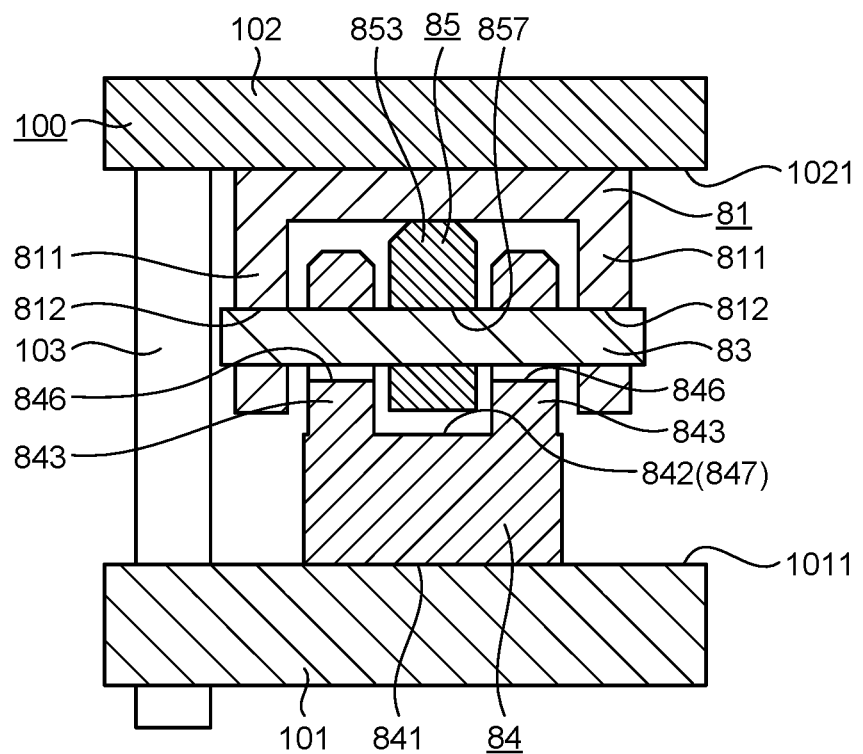
FIG. 10 is a diagram for explaining the method of manufacturing the treatment tool.

FIG. 5 is a flowchart illustrating a method of manufacturing the treatment tool 1. FIG. 6 to FIG. 10 are diagrams for explaining the method of manufacturing the treatment tool. Specifically, FIG. 6 is a cross-sectional view illustrating a state of each of the portions 81, 84, and 85 subjected to Step S1, taken along a plane (hereinafter, described as a first plane) that is perpendicular to the central axis Ax and that passes through the connection region 853. FIG. 7 is a diagram illustrating the holder portion 85 in FIG. 6 when viewed in the width direction (horizontal direction in FIG. 6). FIG. 8 is a cross-sectional view illustrating a state of each of the portions 81, 84, and 85 subjected to Step S2, taken along the first plane. FIG. 9 is a diagram illustrating the holder portion 85 in FIG. 8 when viewed in the width direction (horizontal direction in FIG. 8). FIG. 10 is a cross-sectional view illustrating a state of each of the portions 81, 84, and 85 subjected to Step S3, taken along the first plane.

First, the operator sets the first jaw 81, the treatment portion 84, and the holder portion 85 on an assembly tool 100 as described below (Step S1).

Here, the assembly tool 100 is what is called a vise or the like. Specifically, the assembly tool 100 includes, as illustrated in FIG. 6, a fixing portion 101 having a first surface 1011, a movable part 102 having a second surface 1021, and a slide shaft 103 that connects the fixing portion 101 and the movable part 102 in a posture in which the first surface 1011 and the second surface 1021 face each other. Further, the movable part 102 is movable in a direction approaching or separating from the fixing portion 101 along the slide shaft 103.

Specifically, at Step S1, the operator sets the treatment portion 84 on the fixing portion 101 in a posture in which the first grasping surface 841 comes into contact with the first surface 1011 as illustrated in FIG. 6. Further, the operator sets the holder portion 85 in the first concave portion 847 in a posture in which the first contact surface 854 and the second contact surface 855 come into contact with the opposing surface 842. Furthermore, the operator sets the first jaw 81 above the treatment portion 84 and the holder portion. 85 in a posture in which the treatment portion 84 and the holder portion 85 are located between the pair of side wall portions 811.

Moreover, in the holder portion 85 subjected to Step S1, a depth of the second concave portion 856 corresponds to a first depth D1 as illustrated in FIG. 7. In this state, as illustrated in FIG. 6, the first circular holes 812 and the second circular hole 857 face one another. However, the first circular holes 812 and the second circular hole 857 are located above the first long holes 846 in FIG. 6 and do not face the first long holes 846.

After Step S1, the operator compresses the holder portion 85 as described below (Step S2).

Specifically, at Step S2, the operator operates the assembly tool 100 to bring the movable part 102 close to the fixing portion 101, and the holder portion 85 is compressed to a first state (FIG. 8 and FIG. 9) due to the movement of the movable part 102.

Here, as illustrated in FIG. 8 or FIG. 9, the first state is an elastically deformed state in which the first contact surface 854 and the second contact surface 855 come into contact with the opposing surface 842, and the depth of the second concave portion 856 is reduced to a second depth D2 that is smaller than the first depth D1. Further, in the first state, as illustrated in FIG. 8, the first circular holes 812 and the second circular hole 857 are located at positions facing the first long holes 846. Furthermore, in the first state, as illustrated in FIG. 9, a first angle θ1 formed between a first adjacent surface 8561 that constitutes the second concave portion 856 and that is adjacent to the first contact surface 854 and the first contact surface 854 is an obtuse angle. Similarly, in the first state, a second angle θ2 formed between a second adjacent surface 8562 that constitutes the second concave portion 856 and that is adjacent to the second contact surface 855 and the second contact surface 855 is an obtuse angle.

After Step S2, as illustrated in FIG. 10, the operator inserts the rotation shaft part 83 in the first circular holes 812, the second circular hole 857, and the first long holes 846 (Step S3). Further, the rotation shaft part 83 is hooked on upper edge portions of the first long holes 846, so that the holder portion 85 is prevented from returning to an original shape from the first state (FIG. 9). In other words, the rotation shaft part 83 corresponds to a restricting portion.

Figure 11:
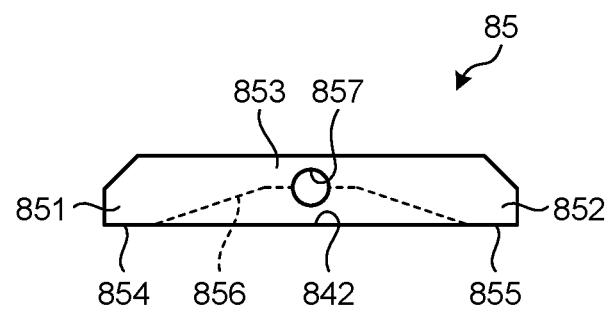
FIG. 11 is a diagram illustrating a state of a holder portion when the target region is grasped.

FIG. 11 is a diagram illustrating a state of the holder portion. 85 when the target region is grasped. Specifically, FIG. 11 is a diagram corresponding to FIG. 7 and FIG. 9.

Further, as described above, the first long holes 846 are long holes that extend in the vertical direction in FIG. 3 and FIG. 4. In other words, the rotation shaft part 83 is hooked on the upper edge portions of the first long holes 846 when moving upward in FIG. 10 from the first state, and therefore is not able to move upward. However, the rotation shaft part 83 is not hooked on edge portions of the first long holes 846 when moving downward in FIG. 10 from the first state, and therefor is able to move by a distance corresponding to the length of each of the first long holes 846 in the longitudinal direction. Therefore, the holder portion 85 is mounted on the treatment portion. 84 such that returning from the first state to the original shape is prevented by the rotation shaft part 83 and elastic deformation from the first state to a posture in which the depth of the second concave portion 856 is reduced is allowed.

Further, in a state in which the target region is grasped between the first grasping surface 841 and the second grasping surface 933, the holder portion 85 is elastically deformed such that the depth of the second concave portion 856 is reduced to almost zero and a bottom surface of the second concave portion 856 that is deformed into an approximately flat shape substantially comes into contact with the opposing surface 842 (FIG. 11).

According to the embodiment as described above, it is possible to achieve effects as described below.

In the treatment tool 1 according to the present embodiment, the holder portion 85 is mounted on the treatment portion 84 such that returning from the first state to the original shape is prevented by the rotation shaft part 83 and elastic deformation from the first state to a posture in which the depth of the second concave portion 856 is reduced is allowed. In other words, in the first state, with the aid of a compression force that is generated along with the elastic deformation of the holder portion 85, a bias is applied to the distal end portion and the proximal end portion of the treatment portion 84 in the longitudinal direction. Therefore, when the target region is grasped between the first grasping surface 841 and the second grasping surface 933, a pressure (grasping force) that is applied to the distal end portion and the proximal end portion of the target region in the longitudinal direction is increased as compared to a conventional structure.

Therefore, according to the treatment tool 1 of the present embodiment, it is possible to make the pressure applied to the entire target region uniform, and realize stable treatment performance.

Furthermore, in the treatment tool 1 according to the present embodiment, the rotation shaft part 83 is adopted as the restricting portion. Therefore, as compared to a configuration in which the restricting portion is arranged separately from the rotation shaft part 83, it is possible to reduce the number of components and simplify the structure.

Moreover, in the treatment tool 1 according to the present embodiment, the first angle θ1 formed between the first adjacent surface 8561 and the first contact surface 854 and the second angle θ2 formed between the second adjacent surface 8562 and the second contact surface 855 are obtuse angles. Therefore, in the state in which the target region is grasped between the first grasping surface 841 and the second grasping surface 933, the holder portion 85 is elastically deformed such that the depth of the second concave portion 856 is reduced to approximately zero and the bottom surface of the second concave portion. 856 that is deformed into an approximately flat shape substantially comes into contact with the opposing surface 842 (FIG. 11). Therefore, it is possible to make the pressure applied to the entire target region uniform.

Another exemplary embodiment will be described below with respect to FIG. 12.

In the following description, the same components as those of the above embodiment as described above are denoted by the same reference symbols, and detailed explanation thereof will be omitted or simplified.

Figure 12:
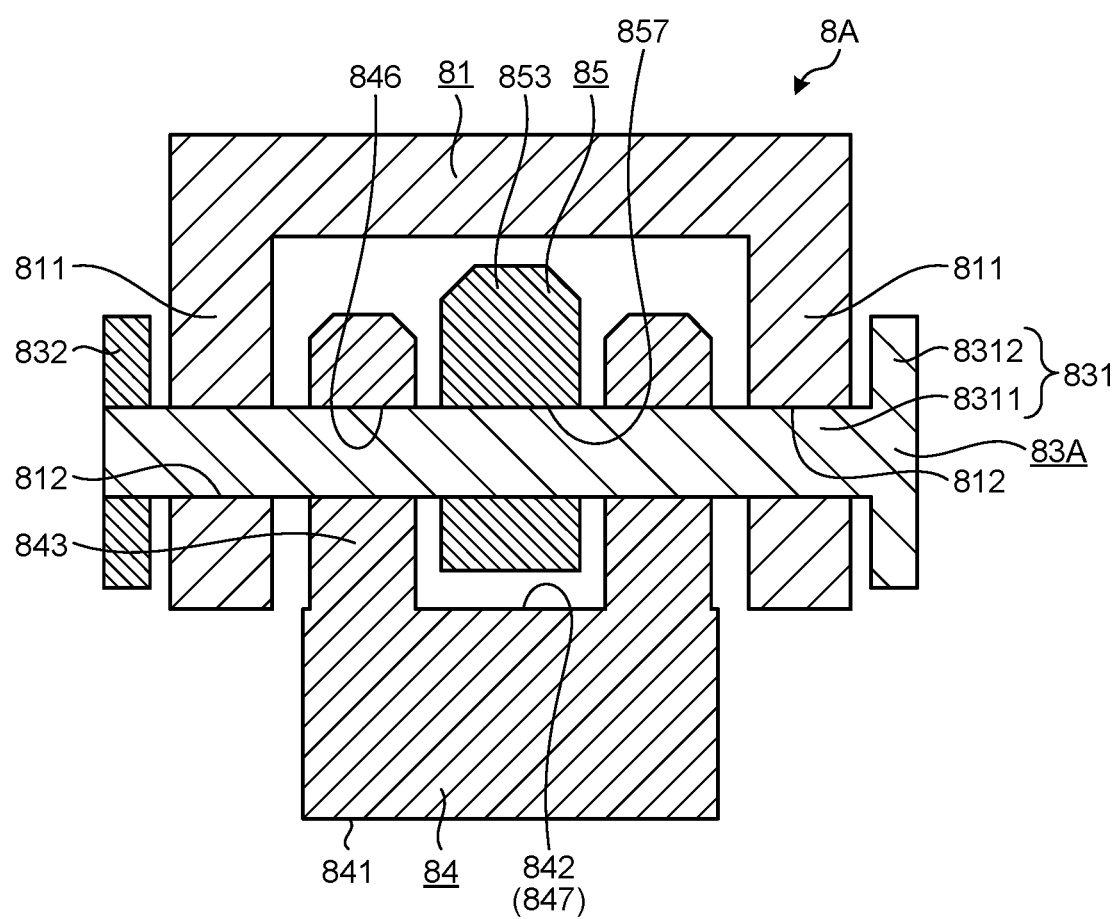
FIG. 12 is a diagram illustrating a first grasper according to an exemplary embodiment.

FIG. 12 is a diagram illustrating a first grasper 8A according to this embodiment. Specifically, FIG. 12 is a cross-sectional view of the first grasper 8A taken along the first plane.

In the first grasper 8A, as illustrated in FIG. 12, a rotation shaft part 83A with a different configuration from the rotation shaft part 83 is adopted in the first grasper 8 that is explained in the embodiment described above.

The rotation shaft part 83A includes, as illustrated in FIG. 12, a shaft part main body 831 in which a flange portion 8312 is arranged on one end of a pin 8311 that has the same shape as the rotation shaft part 83 explained in the embodiment described above, and a fixing portion 832.

The flange portion 8312 is a portion that is projected from an outer peripheral surface of the pin 8311 at one end of the pin 8311.

The fixing portion 832 has the same shape as the flange portion 8312, and is fixed to another end of the pin 8311 by laser welding or the like after the pin 8311 is inserted in the first circular holes 812, the second circular hole 857, and the first long holes 846 at Step S3.

In other words, the flange portion 8312 and the fixing portion 832 prevent the rotation shaft part 83A from coming off from the first circular holes 812, the second circular hole 857, and the first long holes 846.

Even if the rotation shaft part 83A explained in the embodiment as described above with respect to FIG. 12 is adopted, it is possible to achieve the same effects as those of the embodiment discussed with respect to FIGS. 1-11.

Another exemplary embodiment will be described below with respect to FIGS. 13-17.

In the following description, the same components as those of the embodiment as described above are denoted by the same reference symbols, and detailed explanation thereof will be omitted or simplified.

Figure 13:
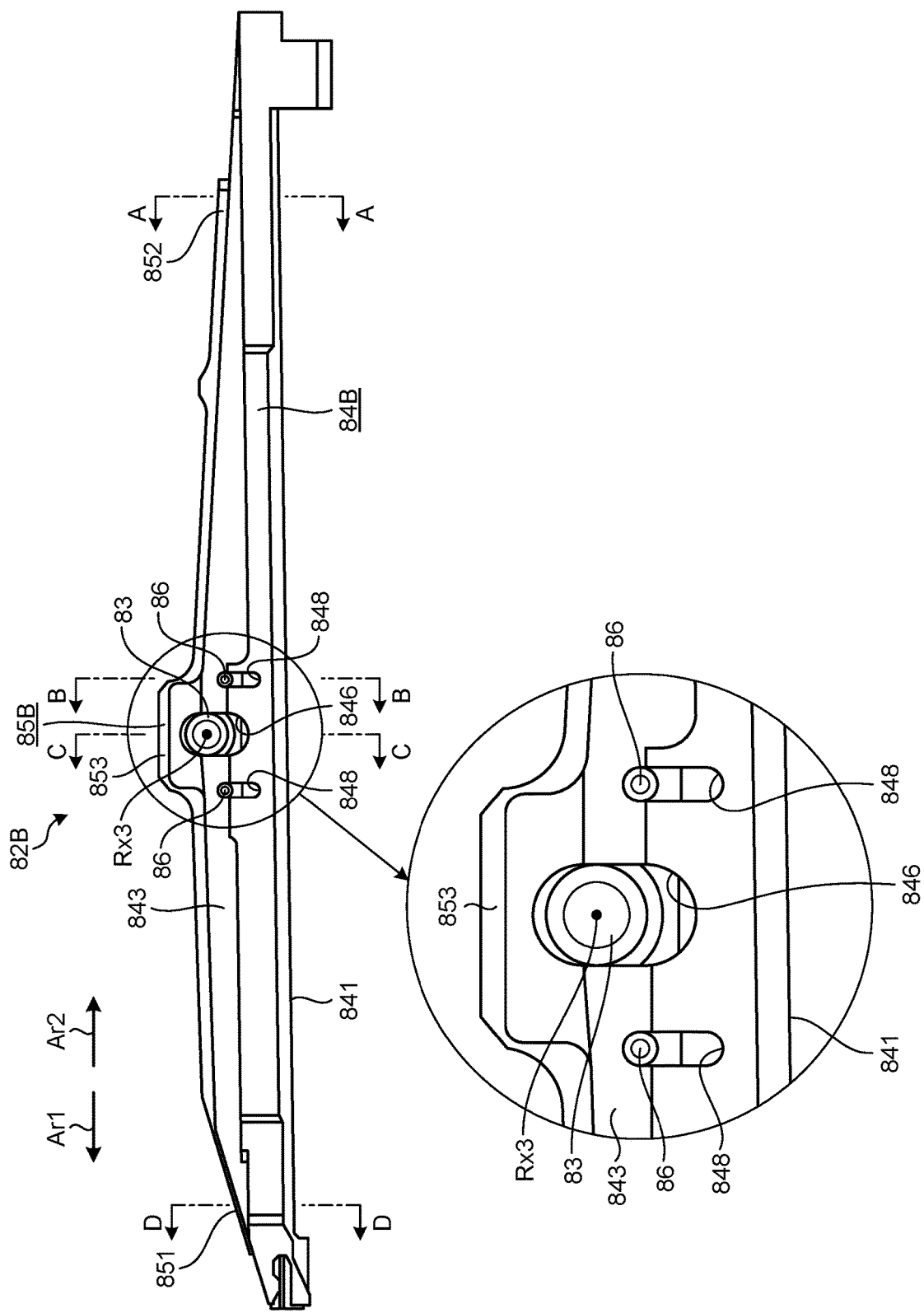
FIG. 13 is a diagram illustrating a configuration of a wiper jaw according to an exemplary embodiment.
Figure 14:
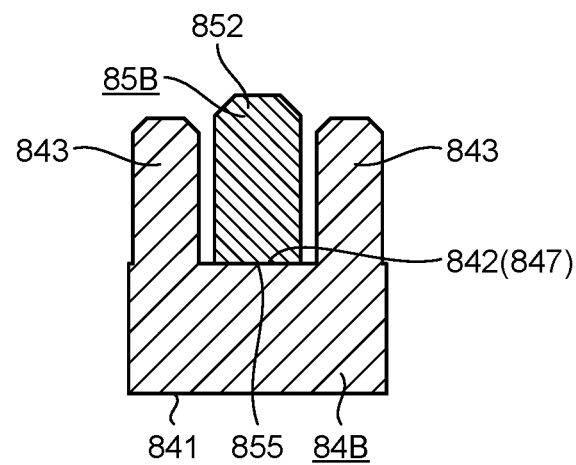
FIG. 14 is a cross-sectional view taken along a line A-A in FIG. 13.
Figure 15:
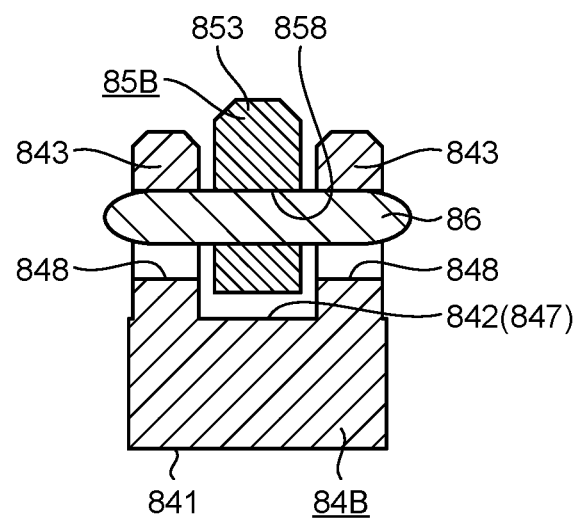
FIG. 15 is a cross-sectional view taken along a line B-B in FIG. 13.
Figure 16:
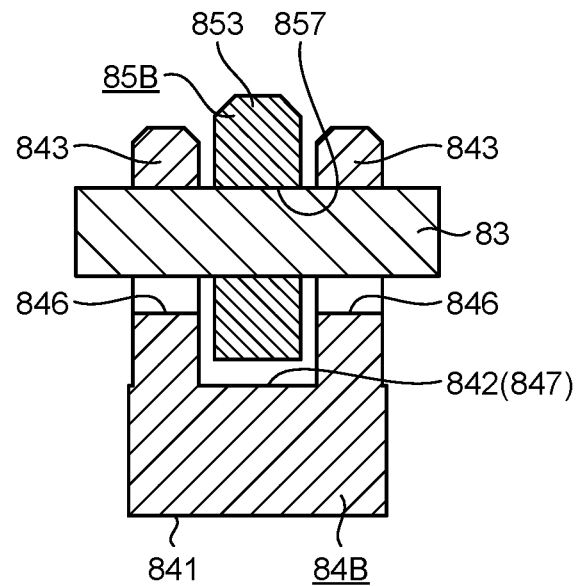
FIG. 16 is a cross-sectional view taken along a line C-C in FIG. 13.
Figure 17:
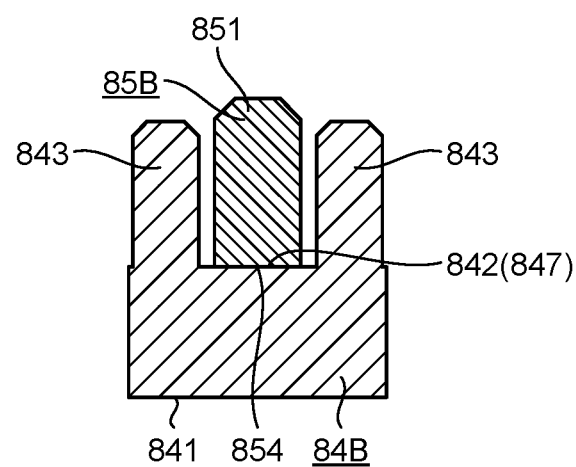
FIG. 17 is a cross-sectional view taken along a line C-C in FIG. 13.

FIG. 13 is a diagram corresponding to FIG. 3, and is a diagram illustrating a configuration of a wiper jaw 82B according to the present embodiment. FIG. 14 is a cross-sectional view taken along a line A-A in FIG. 13. FIG. 15 is a cross-sectional view taken along a line B-B FIG. 16 is a cross-sectional view taken along a line C-C in FIG. 13. FIG. 17 is a cross-sectional view taken along a line D-D in FIG. 13.

In the wiper jaw 82 according to the embodiment as described above with respect to FIGS. 1-11, the rotation shaft part 83 is adopted as the restricting portion.

In contrast, in the wiper jaw 82B according to the present embodiment, a pair of columnar restricting pins 86 (FIG. 13) different from the rotation shaft part 83 is adopted as the restricting portion.

A treatment portion 84B included in the wiper jaw 82B is different from the treatment portion 84 explained in the embodiment described above with respect to FIGS. 1-11 in that a pair of second long holes 848 is arranged as illustrated in FIG. 13 and FIG. 15.

The second long holes 848 as the pair are arranged, in each of the second side wall portions 843 as the pair, at positions on both sides sandwiching each of the first long holes 846. Each of the second long holes 848 is a hole that penetrates through the second side wall portion 843 along a direction perpendicular to the sheet of FIG. 13, has a slightly larger width than an outer diameter size of each of the restricting pins 86, and extends in the vertical direction in FIG. 13 and FIG. 15. Further, the restricting pins 86 are inserted in the second long holes 848.

A holder portion 85B included in the wiper jaw 82B is different from the holder portion. 85 explained in the embodiment described above with respect to FIGS. 1-11 in that a pair of third circular holes 858 are arranged as illustrated in FIG. 13 and FIG. 15.

The third circular holes 858 as the pair are arranged at positions on both sides sandwiching the second circular hole 857. The third circular holes 858 penetrate through the holder portion 85B along the direction perpendicular to the sheet of FIG. 13, and have inner diameter sizes that are slightly larger than the outer diameter sizes of the restricting pins 86, Further, the restricting pins 86 are inserted in the third circular holes 858.

Furthermore, in the present embodiment, at Step S3, the rotation shaft part 83 is inserted in the first circular holes 812, the second circular hole 857, and the first long holes 846, and the restricting pins 86 are inserted in the second long holes 848 and the third circular holes 858.

Moreover, the holder portion 85B is prevented from returning to the original shape (FIG. 7) from the first state (FIG. 9) set at. Step S2 because the restricting pins 86 are hooked on upper edge portions of the second long holes 848 as illustrated in FIG. 13 and FIG. 15. Meanwhile, in the first state, as illustrated in an enlarged view in FIG. 13, the rotation shaft part 83 does not come into contact with upper and lower edge portions of the first long holes 846 and does not prevent the holder portion 85B from returning to the original shape (FIG. 7).

Furthermore, as described above, the second long holes 848 are long holes That extend in the vertical direction in FIG. 13 and FIG. 15. In other words, the restricting pins 86 are hooked on the upper edge portions of the second long holes 848 when moving upward in FIG. 13 from the first state, and therefore are not able to move upward. However, the restricting pins 86 are not hooked on the edge portions of the second long holes 848 when moving downward in FIG. 13 from the first state, and therefore are able to move by a distance corresponding to the length of each of the second long holes 848 in the longitudinal direction. Therefore, the holder portion 85B is mounted on the treatment portion 84B such that returning from the first state to the original shape is prevented by the restriction pins 86, and elastic deformation from the first state to a posture in which the depth of the second concave portion 856 is reduced is allowed.

According to the present embodiment, it is possible to achieve effects as described below, in addition to the effects of the embodiment as described above with respect to FIGS. 1-11.

Meanwhile, if the rotation shaft part 83 is adopted as the restricting portion, a problem as described below may occur in some cases.

With a force that is generated when the holder portion 85 returns from the first state to the original shape, a grasping force is applied to the rotation shaft part in the vertical direction from the edge portions of the first circular holes 812 and the edge portion of the second circular hole 857. Accordingly, when the wiper jaw 82 rotates about the third rotation axis Rx3 relative to the first jaw 81, a friction force is generated between the rotation shaft part 83 and the edge portions of the first circular holes 812 and the second circular hole 857, so that it is difficult for the wiper jaw 82 to smoothly rotate.

In contrast, in the present embodiment, the restriction pins 86 chat are separated from the rotation shaft part 83 are adopted as the restricting portion. Therefore, it is possible to smoothly rotate the wiper jaw 82B about the third rotation axis Rx3 relative to the first law 81.

While the embodiments of the disclosure have been described above, the disclosure is not limited to only the embodiments as described above.

The examples have been explained in the embodiments as described above in which the thermal energy is adopted as the treatment energy to be applied to the target region; however, embodiments are not limited to this example, and it may be possible to adopt high frequency energy, ultrasound energy, or the like. Here, "application of the high frequency energy to the target region" indicates that a high-frequency electric current is caused to flow into the target region. Further, "application of the ultrasound energy to the target region" indicates that ultrasonic vibration is applied to the target region.

Moreover, the treatment tool according to the disclosure need not always be configured to apply the treatment energy to the target region, but may be configured to only grasp the target region (for example, forceps) without applying the treatment energy to the target region.

In the embodiments as described above, the rotation shaft part 83 and the restriction pins 86 are adopted as the restricting portion, but embodiments are not limited to this example, and it may be possible to adopt a different structure as long as it is possible to prevent the holder portions 85 and 85B from returning from the first state to the original shapes. For example, in a configuration in which the holder portions 85 and 85B are mounted on the treatment portions 84 and 84B by snap-fitting, swaging, or the like, it is possible to prevent the holder portions 85 and 85B from returning from the first state to the original shapes.

In the embodiments as described above, the wiper jaws 82 and 82B are configured so as to be rotatable about the third rotation axis Rx3 relative to the first jaw 81, but embodiments are not limited to this example, and the wiper jaws 82 and 82B may be configured so as not to be rotatable. In other words, it may be possible to configure the first law 81 and the holder portions 85 and 85B in an integrated manner.

According to the treatment tool and the method of manufacturing the treatment tool of the disclosure, it is possible to realize stable treatment performance.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment tool comprising:
   a first grasper; and
   a second grasper configured to grasp a living tissue with the first grasper, wherein:
   the first grasper includes:
   a jaw portion that has an elongated shape and is configured to open and close relative to the second grasper,
   a treatment portion that includes: (i) a treatment surface facing the second grasper and (ii) an opposing surface on an opposing side of the treatment surface, and
   a holder portion that is mounted on the opposing surface of the treatment portion,
   the holder portion is formed of an elastically deformable material, and includes:
   a first region having a first contact surface in contact with the opposing surface,
   a second region having a second contact surface in contact with the opposing surface, and
   a connection region that is arranged between the first contact surface and the second contact surface and that includes a concave portion,
   the jaw portion is configured to support the holder portion in the connection region,
   the holder portion is mounted on the opposing surface in an elastically deformed state such that the first contact surface and the second contact surface are in contact with the opposing surface and such that a depth of the concave portion is a second depth that is less than a first depth of the concave portion in a non-elastically deformed state,
   the holder portion is mounted on the opposing surface so as to be capable of further elastic deformation to a state in which the depth of the concave portion is less than the second depth,
   the first grasper includes a restricting portion configured to prevent the holder portion from returning to the first depth from the second depth,
   a pair of side wall portions facing each other across the holder portion is arranged on the opposing surface of the treatment portion,
   the pair of side wall portions each includes a first hole in which the restricting portion is inserted,
   the holder portion includes a second hole in which the restricting portion is inserted, and
   the first hole of each of the pair of side wall portions is a larger hole than the second hole.

2. The treatment tool according to claim 1, wherein:
the restricting portion is a rotation shaft which extends along a first axis, and
the holder portion is mounted on the rotation shaft so as to be rotatable about the first axis relative to the jaw portion.

3. The treatment tool according to claim 2, wherein the rotation shaft includes a shaft main body and a flange portion arranged at one end of the shaft main body.

4. The treatment tool according to claim 1, wherein:
the first grasper further includes a rotation shaft which extends along a first axis, and
the holder portion is mounted on the rotation shaft so as to be rotatable about the first axis relative to the jaw portion.

5. The treatment tool according to claim 4, wherein the rotation shaft includes a shaft main body and a flange portion arranged at one end of the shaft main body.

6. The treatment tool according to claim 1, wherein:
the holder portion further includes:
  a first adjacent surface that is adjacent to the first contact surface and that constitutes the concave portion; and
  a second adjacent surface that is adjacent to the second contact surface and that constitutes the concave portion, and
a first angle formed between the first contact surface and the first adjacent surface is an obtuse angle, and a second angle formed between the second contact surface and the second adjacent surface is an obtuse angle.

7. The treatment tool according to claim 1, wherein the holder portion is configured to be further elastically deformed to the state in which the depth of the concave portion is less than the second depth when a treatment target is grasped between the first grasper and the second grasper.

8. The treatment tool according to claim 1, wherein the concave portion is formed in a surface of the holder portion that faces the opposing surface of the treatment portion and is concave in a direction away from the opposing surface of the treatment portion.

9. A method of manufacturing the treatment tool according to claim 1,
the method comprising:
  arranging the holder portion such that the first contact surface and the second contact surface are in contact with the opposing surface;
  setting the holder portion in a first state in which the holder portion is elastically deformed so that the depth of the concave portion is reduced from the first depth in the non-elastically deformed state to the second depth that is smaller than the first depth; and
  arranging the restricting portion between the treatment portion and the holder portion to prevent the holder portion from returning to the non-elastically deformed state from the first state.

10. A treatment tool comprising:
a first grasper; and
a second grasper configured to grasp a living tissue with the first grasper, wherein:
the first grasper includes:
  a treatment portion that includes: (i) a treatment surface facing the second grasper and (ii) an opposing surface on an opposing side of the treatment surface,
  a holder portion that is mounted on the opposing surface of the treatment portion, and
  a jaw portion that supports the holder portion and the treatment portion such that the holder portion is sandwiched between the jaw portion and the treatment portion in an opening/closing direction of the first grasper and the second grasper,
the holder portion is formed of an elastically deformable material, and includes:
  a first region having a first contact surface in contact with the opposing surface,
  a second region having a second contact surface in contact with the opposing surface, and
  a connection region that is arranged between the first contact surface and the second contact surface and that includes a concave portion,
the holder portion is mounted on the opposing surface in an elastically deformed state such that the first contact surface and the second contact surface are in contact with the opposing surface and such that a depth of the concave portion is a second depth that is less than a first depth of the concave portion in a non-elastically deformed state,
the holder portion is mounted on the opposing surface so as to be capable of further elastic deformation to a state in which the depth of the concave portion is less than the second depth,
the treatment portion includes a pair of side walls that extend from the opposing surface in a direction toward the jaw portion and are arranged on opposite sides of the holder portion in a direction orthogonal to the opening/closing direction of the first grasper and the second grasper,
the pair of side walls each include a first hole,
the connection region of the holder portion includes a second hole that is smaller than the first hole of each of the pair of side walls of the treatment portion, and
a shaft extends through the first hole of each of the pair of side walls of the treatment portion and the second hole of the connection region so as to couple the treatment portion to the holder portion.

11. The treatment tool according to claim 10, wherein the holder portion is compressed between the treatment portion and the jaw portion so be in the elastically deformed state in which the depth of the concave portion is the second depth.

12. The treatment tool according to claim 11, wherein:
the jaw portion includes a second pair of side walls that extend in a direction towards the second grasper and are arranged on opposite sides of the holder portion in the direction orthogonal to the opening/closing direction of the first and second grasper, and
the shaft further extends through a hole formed in each of the second pair of side walls of the jaw portion to couple the jaw portion to the holder portion and the treatment portion.

13. A treatment tool comprising:
a first grasper; and
a second grasper configured to grasp a living tissue with the first grasper, wherein:
the first grasper includes:
  a jaw portion that has an elongated shape and is configured to open and close relative to the second grasper,
  a treatment portion that includes: (i) a treatment surface facing the second grasper and (ii) an opposing surface on an opposing side of the treatment surface,
  a rotation shaft which extends along a first axis, and
  a holder portion that is mounted on the opposing surface of the treatment portion, and is mounted on the rotation shaft so as to be rotatable about the first axis relative to the jaw portion, the holder portion is formed of an elastically deformable material, and includes:
   a first region having a first contact surface in contact with the opposing surface,
   a second region having a second contact surface in contact with the opposing surface, and
   a connection region that is arranged between the first contact surface and the second contact surface and that includes a concave portion,
the jaw portion is configured to support the holder portion in the connection region,
the holder portion is mounted on the opposing surface in an elastically deformed state such that the first contact surface and the second contact surface are in contact with the opposing surface and such that a depth of the concave portion is a second depth that is less than a first depth of the concave portion in a non-elastically deformed state,
the holder portion is mounted on the opposing surface so as to be capable of further elastic deformation to a state in which the depth of the concave portion is less than the second depth,
the first grasper further includes a restricting portion configured to prevent the holder portion from returning to the first depth from the second depth, and
the restricting portion is a restricting pin that extends through a hole formed in each of the holder portion, the jaw portion, and the treatment portion.

\* \* \* \* \*